US009301955B2

(12) United States Patent
Costantini

(10) Patent No.: US 9,301,955 B2
(45) Date of Patent: Apr. 5, 2016

(54) TRITOQUALINE FOR USE IN THE TREATMENT OF CYSTIC FIBROSIS

(71) Applicant: ORPHAN SYNERGY EUROPE-PHARMA, Paris (FR)

(72) Inventor: Dominique Costantini, Paris (FR)

(73) Assignee: ORPHAN SYNERGY EUROPE-PHARMA, Paris (FR)

( * ) Notice: Subject to any disclaimer, the term of this patent is extended or adjusted under 35 U.S.C. 154(b) by 0 days.

(21) Appl. No.: 14/397,743

(22) PCT Filed: Apr. 19, 2013

(86) PCT No.: PCT/EP2013/058158
§ 371 (c)(1),
(2) Date: Oct. 29, 2014

(87) PCT Pub. No.: WO2013/164204
PCT Pub. Date: Nov. 7, 2013

(65) Prior Publication Data
US 2015/0133487 A1 May 14, 2015

(30) Foreign Application Priority Data
Apr. 30, 2012 (EP) .................................... 12305487

(51) Int. Cl.
*A61K 31/4741* (2006.01)
(52) U.S. Cl.
CPC ................... *A61K 31/4741* (2013.01)
(58) Field of Classification Search
CPC .................................................. A61K 31/4741
See application file for complete search history.

(56) References Cited

U.S. PATENT DOCUMENTS

2010/0144718 A1* 6/2010 Nicolaou et al. ........... 514/225.2
2011/0288114 A1 11/2011 Turner

FOREIGN PATENT DOCUMENTS

WO      WO 88/03023      5/1988
WO      WO 2009/155611    12/2009

OTHER PUBLICATIONS

International Search Report for PCT/EP2013/058158 mailed Jun. 17, 2013.
Written Opinion of the International Searching Authority for PCT/EP2013/068158 mailed Jun. 17, 2013.
S. Yuasa et al., "Suppressive Effects of Tritoqualine on Cell Growth and Collagen Secretion in Fibroblasts", Japanese Journal of Pharmacology, vol. 40, No. 2, 1986, pp. 339-341.
K. Umezu et al., "Suppressive Effect of Tritoqualine on the Acceleration of Fibrosis in the Liver", Folia Pharmacologica Japonica, vol. 87, No. 3, 1986, pp. 291-300.
S. Yuasa et al., Thermapeutic Effect of Tritoqualine on Chronic Liver Injury Model in Rats Induced by Carbon Tetrachloride, Folia Pharmacologica Japonica, vol. 85, No. 4, 1985, pp. 249-257.
H. Zimmermann et al., Interleukin-8 is Activated in Patients with Chronic Liver Diseases and Associated with Hepatic Macrophage Accumulation in Human Liver Fibrosis, PLOS One, vol. 6, no. 6, Jun. 2011.

* cited by examiner

*Primary Examiner* — Samantha Shterengarts
(74) *Attorney, Agent, or Firm* — Nixon & Vanderhye P.C.

(57) ABSTRACT

This invention relates to tritoqualine for use in the treatment of cystic fibrosis or any one of its complications. The invention also relates to the method for the treatment of cystic fibrosis or any one of its complications by administering tritoqualine. The invention can be used to improve the condition of individuals with cystic fibrosis.

14 Claims, No Drawings

TRITOQUALINE FOR USE IN THE TREATMENT OF CYSTIC FIBROSIS

This application is the U.S. national phase of International Application No. PCT/EP2013/058158 filed 19 Apr. 2013 which designated the U.S. and claims priority to European Patent Application No. 12 305 487.6 filed 30 Apr. 2012, the entire contents of each of which are hereby incorporated by reference.

FIELD OF THE INVENTION

This invention relates to the field of biology, pharmacy and medicine. It relates in particular to tritoqualine for use in the treatment of cystic fibrosis or any other fibrosis disease associated with IL-8. The invention also relates to the method for the treatment of cystic fibrosis or any other fibrosis disease associated with IL-8 by administering tritoqualine. The invention can be used to improve the condition of individuals with any fibrosis disease associated with IL-8, and in particular cystic fibrosis and any complication thereof.

BACKGROUND TO THE INVENTION

Cystic fibrosis affect 70,000 children and adults worldwide (Cystic fibrosis foundation). Although more than 1,400 different mutations can lead to defects in CFTR, the most common mutation is a deletion of phenylalamine residue at position 508 of the protein (DF508 CFTR). This mutation is responsible for more than 90 percent of CF cases worldwide.

Cystic fibrosis (CF) is an autosomal recessive disorder caused by mutations of the CF transmembrane conductance regulator (CFTR) gene, which encodes a transmembrane protein present on a variety of cell types and organelles. The most common mutation of the CFTR gene is a 3-base-pair deletion resulting in the deletion of phenylalanine at position 508, known as the F508del CFTR mutation. While CF is classically characterized by the presence of pancreatic insufficiency and recurrent lung infections in infants, a wide clinical spectrum has been identified in adults. Chronic bacterial infection of the airways, thickened airway mucous, and bronchiectasis characterizes the CF lung. The excess of mucus is largely caused by the influx of neutrophils, attracted to the site by the increased expression of chemokines such as interleukin-6 (IL-6) and interleukin-8 (IL-8), by bacterial products and inflammatory cytokines.

For instance, IL-8, produced by macrophages, epithelial cells, and fibroblasts, is a potent chemokine and activator for human neutrophils and is considered to be an important proinflammatory cytokine in the pathogenesis of CF (E. Puchelle, S. De Bentzmann, C. Hubeau, J. Jacquot, and D. Gaillard, "Mechanisms involved in cystic fibrosis airway inflammation," *Pediatric Pulmonology*, vol. 32, no. 23, pp. 143-145, 2001). IL-8 is induced transcriptionally by a wide variety of stimuli including tumor necrosis factor-alpha (TNF-α), hyperosmotic shock, and bacterial products. CF causes a massive pro-inflammatory phenotype in the lung, which manifests in the airway by high levels of IL-8 and other pro-inflammatory cytokines and chemokines (Bhattacharyya S. et al., J Biol Chem. 2011 Apr. 1; 286(13):11604-11615). IL8 thus appears to be a major inflammatory cytokine playing a key role in CF, in particular nasal and bronchial CF symptoms.

Progressive lung disease in cystic fibrosis (CF) is largely due to persistent inflammation characterized by an abundance of activated neutrophils. The influx of neutrophils into CF airways has been traditionally thought to be a response to chronic infection with bacteria. However, recent bronchoalveolar lavage (BAL) studies have documented elevated levels of neutrophils in the lower airways of some infants with CF even in the absence of detectable infection. These observations are consistent with the hypothesis that inflammation is abnormally regulated in CF airways. Attention has been focused on interleukin IL-8, a chemokine that accounts for most of the neutrophil chemoattractant activity of CF sputum and is repeatedly found in elevated concentrations in the airways of patients with CF. A potentially major source of IL-8 in the airways is the respiratory epithelium. Since the respiratory epithelium also manifests the most important phenotypic abnormality of CF, CF airway epithelial cells overproduce IL-8, and this is linked to abnormal function of the cystic fibrosis transmembrane regulator (CFTR). IL-8 production in CF and non-CF primary nasal epithelial cell cultures at baseline and after stimulation with tumor necrosis factor-α (TNF-α) or infection by respiratory syncytial virus (RSV) were used as IL-8 models (Nasal epithelium has the same ion transport abnormalities as lower airway epithelium in CF).

Treatments for CF disease typically involve antibiotics, anti-inflammatory drugs, bronchodilators, and chest physiotherapy to help fight infection, neutrophilic inflammation and obstruction and clear the airways. The goal is thus to maintain the lung functions as near to normal by controlling respiratory infection and clearing airways of mucus. Nevertheless, the persistent, viscous and toxic nature of airway secretions in cystic fibrosis disease still leads to progressive deterioration of lung function. Despite its serious clinical consequences, there is no approved therapy for the treatment of CF except ivacaftor (Kalydeco® by Vertex) recently registered in the US and under review in Europe as a cystic fibrosis trans membrane conductance regulator (CFTR) potentiator. Ivacaftor is indicated for the treatment of cystic fibrosis (CF) in patients age 6 years and older who have a G551 D mutation in the CFTR gene. Ivacaftor is only authorized to treat a small sub-set of CF patients, those who have the G551 D mutation in the Cystic Fibrosis Transmembrane Regulator (CFTR) gene and just 4% of CF patients are believed to have this mutation. In addition, sinus related pathology is poorly specifically treated during CF.

No treatment of cystic fibrosis that significantly improves quality of life of patients over a longer period is available so far.

Accordingly, there is a need for alternative or additional treatments for CF and any complication thereof.

7-amino-4,5,6-triethoxy-3-(4-methoxy-6-methyl-7,8-dihydro-5H-[1,3]dioxolo[4,5-g]isoquinolin-5-yl)-3H-isobenzofuran-1-one or tritoqualine is a drug, previously formulated in 100 mg tablets and sold in Europe for the treatment of allergy. Tritoqualine is not a pure product but is available as a mixture of isomers.

The disclosed mechanism of action of tritoqualine relates to the inhibition of histamine biosynthesis. More specifically, tritoqualine is an inhibitor of the enzyme histidine decarboxylase (HDC), which catalyzes histidine decarboxylation in vivo to produce histamine, an endogenous biogenic amine, plus carbon dioxide. Inhibiting histamine production in the body is proposed to ameliorate symptoms of allergy and other diseases that result from high histamine production, such as rhinitis, dermatitis, eczema, urticaria, asthma, . . . . Tritoqualine has also been described in WO2008100539 for the treatment of gastrointestinal disease conditions ameliorated by histamine management, including Gastro-Esophageal Reflux Disease (GERD), a food allergy, Zollinger-Ellison Syndrome, peptic ulcer, dyspepsia, allergic eosinophilic gastroenteritis, and mastocytosis with gastrointestinal symptoms.

In the patent application US20100144718, tritoqualine (TRQ) (including derivatives or isomers thereof) is described as an histamine H4 receptor (H4R) agonist. The application further discloses the use of H4R agonists, such as TRQ, to treat diseases and/or disease conditions modulated by H4R agonists. The H4R modulated disease or condition is more particularly COPD and/or asthma.

SUMMARY OF THE INVENTION

It has been discovered by the inventor that TRQ is a modulator able to decrease the IL8 secretion in inflammatory conditions where epithelial, endothelial, neutrophils, basophils, eosinophils and/or mastocytes cells are more particularly involved. All these cells involved in inflammatory chronic processes are present in lung, nasal and mucosal tissues, CF epithelial cells (multi targeted organs pathology), liver cells and pancreatic cells.

TRQ can thus play a key role in the decrease of IL8 secretion and play a potent anti-inflammatory role in cystic fibrosis conditions.

Surprisingly, TRQ modulation of IL-8 is also active independently of the initial stimulus of the IL-8 release. This impact can be very important in cystic fibrosis where the infection plays an important role on the inflammatory process (IL-8 secretion post stimulus mimicking infection, like Lipopolysacharide (LPS)).

Based on this discovery, the present invention relates to tritoqualine for use in the treatment of cystic fibrosis or at least one of its complications.

The present invention also relates to the use of tritoqualine, for preparing a pharmaceutical composition intended for the treatment of cystic fibrosis or at least one of its complications.

The present invention also relates to a method of treatment of a cystic fibrosis or at least one of its complications, in which a therapeutically effective amount of a tritoqualine is administered to a subject in need of such treatment.

DETAILED DESCRIPTION OF THE INVENTION

Tritoqualine (or TRQ), as mentioned before, is a drug previously on the market for the treatment of allergy. It has the following formula:

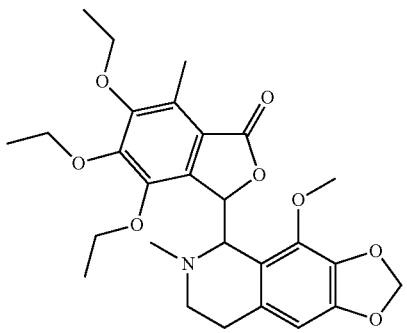 [SMILES: CCOc1c(C)c2c(c(OCC)c1OCC)C(C1c3c(cc4c(c3OC)OCO4)CCN1C)OC2=O]

In the present invention, the term tritoqualine (or TRQ) includes enantiomers, diastereoisomers and/or any mixture thereof. Indeed, and as described in WO2007/117704, the chemical structure of tritoqualine presents two asymmetric carbons. Thus, depending on the method of synthesis, tritoqualine active pharmaceutical ingredient can be produced as either one or two diastereomeric structures each one comprising of its corresponding two mirror images, enantiomers. Thus, tritoqualine can exist as either two or four possible isomeric structures. Using the convention of R and S designation in each asymmetric carbon, one of the two possible diastereomeric structures will be comprised of the RR and SS enantiomers, and the other of RS and SR enantiomers. The term tritoqualine in the present invention also includes any pharmaceutically salt or hydrated form thereof.

As used herein, "pharmaceutically acceptable salt" refers to derivatives of the disclosed TRQ wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

Clinically, Cystic Fibrosis (CF) can present several types of complications. For instance, defective CFTR results in decreased secretion of chloride and increased reabsorption of sodium and water across epithelial cells. The resultant reduced height of epithelial lining fluid and decreased hydration of mucus results in mucus that is stickier to bacteria, which promotes infection and inflammation. Secretions in the respiratory tract, pancreas, gastrointestinal (GI) tract, sweat glands, and other exocrine tissues have increased viscosity, which makes them difficult to clear.

Most patients with cystic fibrosis have severe chronic lung disease and/or exocrine pancreatic insufficiency. Additional manifestations include the following: nasal polyposis, pansinusitis, chronic diarrhea, pancreatitis, cirrhosis or other forms of hepatic dysfunction.

Patients with cystic fibrosis may also have sinus disease: chloride ions cannot be excreted, sodium is excessively absorbed, and water passively follows. This desiccates the mucosal surface and alters the viscosity of the normal mucus blanket, which alone can lead to obstruction of sinus ostia. Additional abnormalities may exist in CF patients, including ciliary dysfunction, increased inflammatory mediators, and increased colonization with *Pseudomonas aeruginosa*, all of which further impair normal sinus clearance and aeration. Chronic sinus infection and inflammation are the net result.

Most deaths associated with cystic fibrosis result from progressive and end-stage lung disease. In individuals with cystic fibrosis, the lungs are normal in utero, at birth, and after birth, before the onset of infection and inflammation. Shortly after birth, many persons with cystic fibrosis acquire a lung infection, which incites an inflammatory response leading to bacterial persistence with production of the neutrophil chemoattractant interleukin IL-8 from epithelial cells and elastin degradation contributing to persistence of inflammation and infection, structural damage, impaired gas exchange, and, ultimately, end-stage lung disease and early death.

Most patients with cystic fibrosis (90-95%) have pancreatic enzyme insufficiency and present digestive disorders with poor weight gain in association with frequent stools and colicky pain after feeding. Pancreatic insufficiency decreases the absorption of intestinal contents adhesion and mechanical intestinal obstruction.

Diabetes is a common complication of adults CF. The main cause of CF related diabetes is destruction of the pancreas due to fibrosis. Islet cells which produce insulin are therefore depleted. In fact, most adults living with CF have some degree of diabetes or glucose intolerance.

Hepatobiliary problems in cystic fibrosis are also frequent including specific focal biliary cirrhosis, resulting from biliary obstruction and progressive periportal fibrosis.

In a particular embodiment, the invention concerns tritoqualine for use in the treatment of cystic fibrosis disease and/or associated complications, said complications include more specifically infection, inflammatory disorder (more specifically in the respiratory tract, pancreas, gastrointestinal (GI) tract, sweat glands, or other exocrine tissues), severe chronic lung disease, pancreatic insufficiency, nasal polyposis, pansinusitis, chronic diarrhea, pancreatitis, cirrhosis or other forms of hepatic dysfunction, sinus disease (e.g., chronic sinus infection and/or inflammation), diabetes, or hepatobiliary problems (e.g., focal biliary cirrhosis, biliary obstruction and progressive periportal fibrosis).

In a particular embodiment, the invention concerns tritoqualine for use in the treatment of cystic fibrosis disease and/or any of airway or nasal associated complications, such as lung disease (e.g., severe chronic lung disease), nasal polyposis, pansinusitis, or sinus disease (e.g., chronic sinus infection and/or inflammation).

The invention further provides methods for the treatment of cystic fibrosis or complications thereof (as identified above) in a subject in need of such treatment, wherein said methods comprise administering to the subject an effective amount of TRQ.

The invention further provides a use of tritoqualine for the preparation of a medicament or a pharmaceutical composition intended for the treatment of cystic fibrosis or at least one of its complications (as identified above).

Within the context of the invention, the term <<treatment>> designates preventive, curative and palliative treatment, as well as the care of patients, improvement of quality of life, reduction of suffering, improvement of life span, deceleration of the progression of the disease, relief of the symptoms, decrease of the effects of the disease for example, by causing regression, or restoring or repairing a lost, missing, or defective function, etc.

Furthermore, the treatment can be carried out in combination with other agents or treatments.

As used herein, the terms "subject", "individual," "animal," and "patient," used interchangeably herein, refer to mammals, including humans, and also include, but are not limited to, murines, simians, felines, canines, equines, bovines, porcines, ovines, caprines, rabbits, mammalian farm animals, mammalian sport animals, and mammalian pets. In many embodiments, the subjects will be humans. Animal models can be of interest for experimental investigations, providing a model for treatment of human disease.

The term "desirable therapeutic effect" means to treat a subject with TRQ to prevent or ameliorate a disease and/or disease condition.

The term "effective amount" means an amount of TRQ or composition according to the present invention effective in producing the desired therapeutic effect.

A dose of Tritoqualine administered to a subject may be about 1, 5, 10, 20, 30, 50, 100, 200, 300, 400, 500, 600 mg/day. In another embodiment, the dose of TRQ administered to a subject may be about 1 g/day. In an additional embodiment, the dose of TRQ administered to a subject may be about 2 g/day. In yet another embodiment, the dose of TRQ administered to a subject may be about 3 g/day. In a further embodiment, the dose of TRQ administered to a subject may be about 1 mg-4 g/day. The expert can adapt the administered doses. It goes without saying that repeat administrations can be implemented, possibly in combination with other active agents or any vehicle which is pharmaceutically acceptable (e.g., buffers, saline solutions, isotonic, in the presence of stabilising agents, etc.).

The phrase "pharmaceutically acceptable" is employed herein to refer to those compounds, materials, compositions; and/or dosage forms which are, within the scope of sound medical judgment, suitable for use in contact with the tissues of the subject without excessive toxicity, irritation, allergic response, or other problem or complication commensurate with a reasonable benefit/risk ratio.

The TRQ used within the framework of this invention is generally formulated in a pharmaceutical composition comprising a pharmaceutically acceptable vehicle or excipient. In a further embodiment, the present invention deals with a pharmaceutical composition comprising TRQ and a pharmaceutically acceptable vehicle or excipient, for use in the treatment of cystic fibrosis or at least one of its complications (as defined above).

It can be administered topically, intravenously, subcutaneously, by inhalation or by using a nebulizer or in orally available form like tablets or capsules, more specifically orally or by inhalation. The administration can be carried out by any method known to experts in the field, preferably orally, by inhalation or injection, which is systemic or local (intra nasal and/or bronchial inhaled forms). The injection is typically administered via the intra-ocular, intra-peritoneal, intra-cerebral, intravenous, intra-arterial, sub-cutaneous or intra-muscular route. Aerosolized delivery of the TRQ may result in a more homogeneous distribution of the active ingredient in a lung, so that deep lung delivery is obtained. Thereby the dosage of application might be reduced to the sustained presence of TRQ at the site of action in the lung.

The pharmaceutical compositions comprising TRQ according to the invention can therefore be presented in the form of tablets, solutes or injectable suspensions or multidose bottles, capsules, pills, cachets, powders, suppositories or rectal capsules, solutions or suspensions.

The pharmaceutically acceptable vehicle or excipient can be chosen from buffer, solvent, binding, stabilising, emulsifying solutions, etc. Buffer or thinning solutions are in particular calcium phosphate, calcium sulphate, lactose, cellulose, kaolin, mannitol, sodium chloride, starch, caster sugar and hydroxypropyl methyl cellulose (HPMC) (for delayed liberation). Binders are for example starch, gelatine and packing solutions such as sucrose, glucose, dextrose, lactose, etc. Natural or synthetic gums can also be used, such as in particular alginate, carboxymethyl cellulose, methyl cellulose, polyvinyl pyrrolidone, etc. Other excipients are for example cellulose, magnesium stearate, cyclodextrins or a mixture thereof. Stabilising agents can be incorporated into the formulations, such as for example polysaccharides (acacia, agar, alginic acid, guar gum and tragacanth, chitin or its derivatives and cellulose ethers). Solvents or solutions are for example Ringer's solution, water, distilled water, phosphate buffers, phosphated saline solutions, and other conventional fluids.

Other aspects and advantages of this invention will become clear from reading the following examples, which must be considered as illustrative and not limiting.

EXAMPLES

Tritoqualin effect on IL8 release on a human ex vivo model (epithelial Cells from Human gingival extraction maintained in survival) after stimulation of IL8 release 1) Preparation of Gingival Mucosa 13 fragments of gingival mucous from different human donors (removal of wisdom teeth of healthy volunteers) were maintained in survival ex vivo. To this end, fragments were placed in inserts themselves willing suspended above the culture wells. The nutrient medium (antibiotics, FCS—Fetal Calf Serum) was added to the bottom of the wells, passage is carried out by slow diffusion of the two compartments by means of a porous membrane (0.45 mm). The whole was maintained in organ culture for 24 hours in an oven to a humid atmosphere at 37° C. in the presence of 5% $CO_2$.

2) Experimental Model of Gingival Mucosa Stimulated by Substance P

Gingival inflammation was achieved by stimulation of the mucosa with a neurotransmitter, substance P (10 microM) deposited in the culture medium. Tritoqualine was added to the culture medium (systemic effect) at a concentration of 20 microM, 10 minutes after application of substance P.

A comparison of the modulation of inflammation (IL8 cytokine dosages) is established in:

gingival mucosa control
gingival mucosa stimulated by substance P,
gingival mucosa stimulated by substance P and TRQ The inflammatory cytokine, IL8, a potent chemo attractant of neutrophils, was measured in culture supernatants, 24 hours after deposition of substance P.

3) Biochemical Assay of a Proinflammatory Cytokine

IL8 was measured in ng/ml by immunoassays (kits Gen Probe, France) with a spectrophotometer at 450 nm.

4) Results and Comments

Substance P increase significantly the IL8 release: 31.7 ng/ml versus 29.6 ng/ml in the control group (p=0.04).

Tritoqualine induces a significant decrease of IL8 release when the mucosal epithelium was stimulated by Substance P (26.7 ng/ml versus 31.7 ng/ml in the group stimulated by the SP (p=0.02).

The human mucosal cells were previously stimulated by Substance P, an established pro-inflammatory compound able to increase significantly the IL8 release on epithelial cells but also on other bronchial or nasal cells. In this context, Tritoqualine has thus demonstrated a significant impact on IL8 release in the ex vivo human epithelial cells model. Tritoqualine, as a new anti-inflammatory property through IL8 decrease, is thus particularly interesting in airways Cystic Fibrosis chronic conditions where IL8 is continually increased.

The invention claimed is:

1. A method for the treatment of cystic fibrosis in a subject in need of such treatment, wherein said method comprises administering to said subject an effective amount of tritoqualine.

2. The method according to claim 1, wherein tritoqualine is administered to the subject in need of such treatment at a dose of 1 mg-4 g/day.

3. The method according to claim 1, wherein tritoqualine is administered to the subject in need of such treatment at a dose of 1, 5, 10, 20, 30, 50, 100, 200, 300, 400, 500, or 600 mg/day.

4. The method according to claim 1, wherein tritoqualine is administered to the subject in need of such treatment at a dose of 1 g/day, 2 g/day, 3 g/day or 4 g/day.

5. A method for the treatment of any complication of cystic fibrosis in a subject with cystic fibrosis, wherein said method comprises administering to said subject an effective amount of tritoqualine.

6. The method according to claim 5, wherein the cystic fibrosis complications are selected from infection or inflammatory disorders.

7. The method according to claim 5, wherein the cystic fibrosis complications are selected from infection or inflammatory disorders in the respiratory tract, pancreas, gastrointestinal tract, sweat glands, or other exocrine tissues.

8. The method according to claim 5, wherein the cystic fibrosis complications are selected in the group consisting of severe chronic lung disease, pancreatic insufficiency, nasal polyposis, pansinusitis, chronic diarrhea, pancreatitis, cirrhosis or other forms of hepatic dysfunction, sinus disease, diabetes, and hepatobiliary problems.

9. The method according to claim 5, wherein the treatment is the treatment of any of airway or nasal complications associated with cystic fibrosis.

10. The method according to claim 5, wherein the treatment is a treatment of any of airway or nasal complications associated with cystic fibrosis and wherein the airway or nasal complications associated with cystic fibrosis is selected from the group consisting of lung disease, nasal polyposis, pansinusitis, and sinus disease.

11. The method according to claim 5, wherein the cystic fibrosis complications are selected from the group consisting of focal biliary cirrhosis, biliary obstruction and progressive periportal fibrosis.

12. The method according to claim 5, wherein tritoqualine is administered to the subject in need of such treatment at a dose of 1 mg-4 g/day.

13. The method according to claim 5, wherein tritoqualine is administered to the subject in need of such treatment at a dose of 1, 5, 10, 20, 30, 50, 100, 200, 300, 400, 500, or 600 mg/day.

14. The method according to claim 5, wherein tritoqualine is administered to the subject in need of such treatment at a dose of 1 g/day, 2 g/day, 3 g/day or 4 g/day.

* * * * *